(12) United States Patent
Chen et al.

(10) Patent No.: US 9,255,078 B2
(45) Date of Patent: Feb. 9, 2016

(54) MICHELIOLIDE DERIVATIVES, MEDICINAL COMPOSITION, PRODUCING METHOD AND USAGE THEREOF

(71) Applicants: ACCENDATECH, Tianjian (CN); NANKAI UNIVERSITY, Tainjin (CN)

(72) Inventors: Yue Chen, Tainjin (CN); Quan Zhang, Tainjin (CN); Yaxin Lu, Tainjin (CN); Jiadai Zhai, Tainjin (CN); Yahui Ding, Tainjin (CN); Jing Long, Tainjin (CN); Hongxia Fan, Tainjin (CN); Haoliang Zhang, Tainjin (CN); Miao Wang, Tainjin (CN); Weiwei Ma, Tainjin (CN)

( * ) Notice: Subject to any disclaimer, the term of this patent is extended or adjusted under 35 U.S.C. 154(b) by 258 days.

(21) Appl. No.: 13/642,516

(22) Filed: Oct. 19, 2012

(65) Prior Publication Data
US 2013/0109749 A1 May 2, 2013

Related U.S. Application Data

(63) Continuation-in-part of application No. PCT/CN2011/072782, filed on Apr. 14, 2011.

(30) Foreign Application Priority Data

Apr. 23, 2010 (CN) .......................... 2010 1 0153701
Oct. 18, 2010 (CN) .......................... 2010 1 0510726

(51) Int. Cl.
| | |
|---|---|
| C07D 307/93 | (2006.01) |
| A61K 31/365 | (2006.01) |
| C07D 493/04 | (2006.01) |
| A61K 45/06 | (2006.01) |
| C07D 493/10 | (2006.01) |

(52) U.S. Cl.
CPC ............ *C07D 307/93* (2013.01); *A61K 31/365* (2013.01); *A61K 45/06* (2013.01); *C07D 493/04* (2013.01); *C07D 493/10* (2013.01)

(58) Field of Classification Search
CPC .. C07D 493/04; C07D 493/10; A61K 31/365; A61K 45/06
See application file for complete search history.

(56) References Cited

FOREIGN PATENT DOCUMENTS

| | | |
|---|---|---|
| CN | 101978959 A | 2/2011 |
| CN | 201010510726.1 | 2/2011 |
| CN | 201010153701.0 | 4/2011 |
| CN | 102234259 A | 11/2011 |
| EP | 2011771556 | 2/2013 |
| JP | 2013-525312 | 6/2013 |
| KR | 10-2013-0029380 | 3/2013 |
| WO | PCT/CN2011/072782 | 10/2011 |

OTHER PUBLICATIONS

Bargues et al. Disclose in Journal of Natural Products 65, 1703-1706 (2002).*
Bargue et al. In Journal of Natural Products, 65, 1703-1706 (2002).*
Ogura et al. In Phytochemistry 17, 957-961 (1978).*
J. G. Cannon Chapter Nineteen in Burgers Medicinal Chemistry and Drug Discovery, Fifth Edition, vol. I: Principles and Practice, Wiley-Interscience 1995, pp. 783-802, 784.*
PCT/072782 Prelim Report, Oct. 27, 2012, Accenda Tech & Nankai Uni.
PCT/072782 Written Opinio, Oct. 27, 2012, Accenda Tech & Nankai Uni.
Masuru Ogura et al., Anticancer Sesquiterpene Lactones of *Michelia compressa* (magnoliaceae), Phytochemistry, 1978, vol. 17 pp. 957-961, Permaon Press Ltd., England.
Felix J. Paroday, et al., Biometric Transformations of 11,13-dihydroparthenolide and Oxidative Rearrangements of a GUI-1(10)-en-6,12-olide, Journal of Natural Products vol. 52, No. 3, pp. 554-566, May-Jun. 1989.
EP 2011771556 Office Action dated Sep. 2, 2013.

* cited by examiner

*Primary Examiner* — Dennis Heyer
(74) *Attorney, Agent, or Firm* — Zareefa B. Flener; Flener IP Law

(57) ABSTRACT

The present invention provides a compound of formula (I)

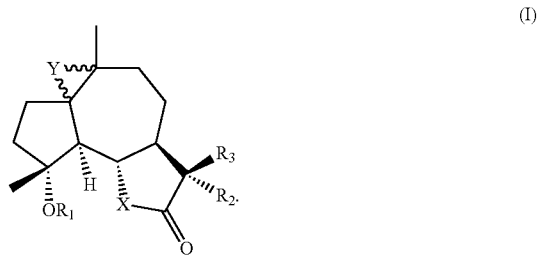

4 Claims, No Drawings

MICHELIOLIDE DERIVATIVES, MEDICINAL COMPOSITION, PRODUCING METHOD AND USAGE THEREOF

CROSS-REFERENCE TO RELATED APPLICATION

The application is a continuation in part of PCT/CN2011/072782 (filed on Apr. 14, 2011), which claims priority of Chinese patent application 201010153701.0 (filed on Apr. 23, 2010) and priority of Chinese patent application 201010510726.1 (filed on Oct. 18, 2010), the contents of which are incorporated herein by reference.

FIELD OF THE INVENTION

The present invention relates to pharmaceutical technology, and more specifically, relates to micheliolide derivatives or salt thereof, and pharmaceutical composition using which as the effective ingredient for the cancer treatment or auxiliary swelling treatment, producing methods thereof, and the usage of the compound and composition in producing anti-cancer or auxiliary anti-cancer drugs.

BACKGROUND OF THE INVENTION

Tumor threats the human health seriously. There are about 200 million cancer patients in China and the number is added by 1.6 million per year, which is a big group. The anti-cancer research is a challenging and significant field in life science and technology. At present, the commonly used clinical anti-cancer drugs are cytotoxic drugs. The characteristics of these drugs are poor selectivity, strong side effects, drug resistance and so on. They are a typical double-edged sword drugs, and difficult to eradicate cancer, which result in high proportion of cancer recurrence. The high rate of the recurrence of cancer has troubled the doctors, and more and more studies confirm that there are a few tumor stem cells in the tumor cell population which can amplify the cell groups. Tumor stem cells are usually in a slow cycle status and have low sensitivity to chemotherapeutic drugs. They are the source of tumor recurrence. The found of the tumor stem cell makes a new target for cancer treatment, and the drug research focused on the tumor stem cell may be able to cure cancer completely.

In recent years, investigations on anti-cancer compounds from natural products have become the hotspot of anti-cancer drug development. For the past 20 years, 61% new small molecule entities drugs may be derived from natural products. Natural products are very common in some therapeutic areas: 78% of the antibacterial compounds and 74% of anti-tumor compounds are natural products or derived from natural products. Practice has proved that the unique role of natural products in anticancer drug discovery re-attach great attention. The traditional treatment of cancer chemotherapy drug have resistance problem, especially the low sensitivity to tumor stem cells. Traditional Chinese medicine (TCM) is profound in anti-cancer field, high efficiency and low toxicity. Accordingly, there is high chance to find drugs eradicating cancer stem cells for cure of malignant tumor from TCM.

Parthenolide, a sesquiterpene lactone extracted from *Tanacetum Parthenium*, was originally used to treat skin infections, rheumatism, and migraine. Recent studies have shown that parthenolide can inhibit the growth of cancer cells, such as prostate cancer, breast cancer, gastric cancer, leukemia, kidney cancer, lung cancer, colon adenocarcinoma, and medulloblastoma. Furthermore, parthenolide is effective on treatment of UV-induced skin cancer in animal model. The study of its mechanism finds that parthenolide can inhibit the activation of the transcription factor NF-κB. The activity was mainly derived from the thiol on the subunit of p65/NF-κB which conducts Michael addition reaction with parthenolide. NF-κB is a key gene to regulate tumor invasion, metastasis, and drug resistance genes; therefore, inhibition of NF-κB activation may increase the sensitivity of tumor apoptosis to tumor inhibitor. Recently, Ph.D. Jordan, C. T. and his colleagues found that parthenolide can selectively eliminate cancer stem cells without damage of normal stem cells, which make it possible to suppress recurrence AML. This unique mechanism action of parthenolide has attracted widespread attention.

Micheliolide belongs to guaiane-type sesquiterpene lacones. It has been reported in the literature [J. Nat. Prod. 1993, 56, 90-98; Bioorg. Med. Chem. Lett. 2003, 11, 1503-1510]. On the basis of the results, the present invention reports the use of micheliolide derivatives and its salts in the cancer treatment.

SUMMARY OF THE INVENTION

The embodiments of present invention provides micheliolide derivative, an anti-cancer pharmaceutical composition comprising an effective amount of micheliolide derivative formula (I) or their salts, methods of preparing them, and the use of micheliolide derivative formula (I) or their salts, or their pharmaceutical composition for preparing anticancer drugs.

To achieve the above-mentioned objectives, technical scheme provided includes:

A compound or salt thereof of formula (I) is provided,

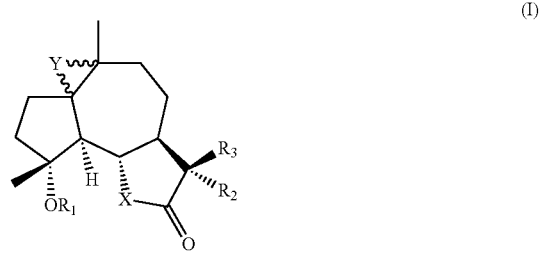

(I)

Wherein:

$R_1$ is H, —C(O)$R_4$ or —C(O)$R_5R_6$, where $R_5$ and $R_6$ are the same or different, $R_4$, $R_5$ and $R_6$ are hydrogen, alkyl, cycloalkyl, alkenyl, alkynyl, aryl, alkyaryl, arylakyl, arylalkenyl, arylalkynyl and heterocyclic;

$R_2$=$R_3$ is double bond, or $R_3$ is hydrogen, $R_2$ is alkyl having in the range of 1 up to 8 carbon atoms containing substitute, where the substituent is selected form cycloalkyl, heterocycloalkyl, aryl, heteroaryl, amino acid fragment, or —$NR_7R_8$, and its pharmaceutically acceptable salts formed with inorganic and/or organic acid and its quaternary ammonium salts formed with $R_9Z$. Preferred substituents are amino acid fragment and methylene substituted by —$NR_7R_8$;

where $R_7$ and $R_8$ are the same or different, they are hydrogen, alkyl, cycloalkyl, alkyl substituted by hydroxyl, alkenyl, alkynyl, aryl, alkyaryl, arylakyl, arylalkenyl, arylalkynyl, heterocyclic, trifluoromethyl, perfluoroalkyl, cyano, cyanomethyl, carboxyl, cabamate, sulfonyl, sulfonamide or aryloxyalkyl; or $R_7$ and $R_8$ together with N form a ring, the ring number is preferable 3-9, the ring can have one or more substituents on it, substituents are selected from hydrogen, alkyl, cycloalkyl, alkenyl, alkynyl, aryl, alkyaryl, arylakyl, arylalkenyl, arylalkynyl and heterocyclic, $R_7$ and $R_8$ are preferably selected from hydrogen, alkyl having in the range of 1 up to 8 carbon atoms, or cycloalkyl;

Z is fluorine, chlorine, bromine, iodine, tosylate, methanesulfonate, benzenesulfonate, trifluoromethanesulfonate, R9 is alkyl, cycloalkyl, alkyl substituted by hydroxyl, alkenyl, alkynyl, aryl, heterocyclic, arylakyl, arylalkenyl, arylalkynyl, cyanomethyl, alkoxy or aryloxyalkyl; inorganic or organic acid are hydrofluoric acid, hydrochloric acid, hydrobromic acid, hydriodic acid, sulfuric acid, nitric acid, phosphoric acid, carbonic acid, boric acid, selenious acid, phosphomolybdic acid, phosphorous acid, sulfurous acid, citric acid, maleic acid, D-malic acid, L-malic acid, DL-malic acid, L-lactic acid, D-lactic acid, DL-lactic acid, oxalic acid, methanesulfonic acid, valeric acid, oleic acid, lauric acid, para-toluenesulfonic acid, 1-naphthalensulfonic acid, 2-naphthalensulfonic acid, phthalic acid, tartaric acid, malonic acid, succinic acid, fumaric acid, glycolic acid, thioglycolic acid, glycine, sarcocine, sulfonic acid, nicotinic acid, picolinic acid, isonicotinic acid, benzoic acid and substituted benzoic acid;

X is O or $R_{10}N$, $R_{10}$ is hydrogen, alkyl, cycloalkyl, alkenyl, alkynyl, aryl, alkyaryl, arylakyl, arylalkenyl, arylalkynyl or heterocyclic;

Y is single bond, O, $R_{11}N$, $R_{12}R_{13}C$, $R_{11}$ is hydrogen, alkyl, cycloalkyl, alkenyl, alkynyl, aryl, alkyaryl, arylakyl, arylalkenyl, arylalkynyl or heterocyclic; $R_{12}$ and $R_{13}$ are the same or different, they are hydrogen, fluorine, chlorine, bromine, iodine, alkyl, cycloalkyl, alkyl substituted by hydroxyl, alkenyl, alkynyl, aryl, heterocyclic, arylakyl, arylalkenyl, arylalkynyl, cyanomethyl, alkoxy or aryloxyalkyl.

Herein, $R_1$ being H, Y being single bond in not compatible with $R_2=R_3$ being double bond.

Preferably, $R_2$ is methylene substituted by $-NR_7R_8$ or amino acid fragment, where $R_7$ and $R_8$ are the same or different, they are hydrogen, alkyl, cycloalkyl, alkyl substituted by hydroxyl, alkenyl, alkynyl, aryl, alkyaryl, arylakyl, arylalkenyl, arylalkynyl, heterocyclic, trifluoromethyl, perfluoroalkyl, cyano, cyanomethyl, carboxyl, cabamate, sulfonyl, sulfonamide or aryloxyalkyl; or $R_7$ and $R_8$ together with N form a ring, the ring number is preferable 3-9, the ring can have one or more substituents on it, substituents are selected from hydrogen, alkyl, cycloalkyl, alkenyl, alkynyl, aryl, alkyaryl, arylakyl, arylalkenyl, arylalkynyl and heterocyclic, $R_7$ and $R_8$ are preferably selected from hydrogen, alkyl having in the range of 1 up to 8 carbon atoms, or cycloalkyl.

The invention also provide a method of producing a compound or salt thereof of formula (I), including: considering micheliolide as material, adding catalyst into organic solvent, and reacting the organic solvent with the catalyst and the material having the corresponding group or structure to obtain the target compound.

Preferably, a compound or salt thereof of formula (I) is represented by formula (II), formula (III), formula (IV), or formula (V)

(II)

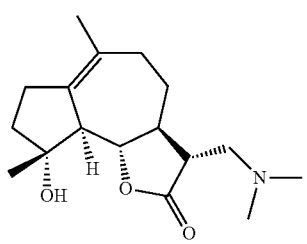

(III)

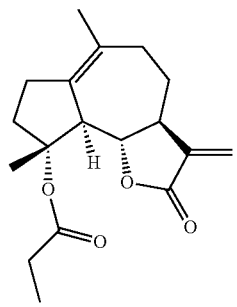

(IV)

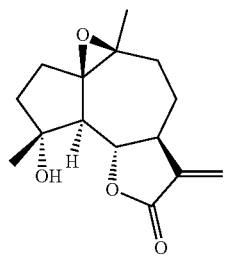

(V)

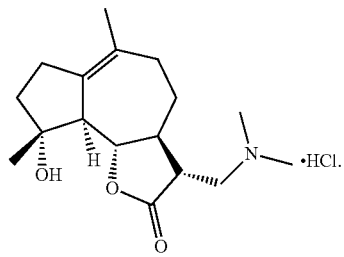

Specifically, the invention provides a method of producing micheliolide derivative of formula (II), comprising: reacting materials to obtain the target compound, wherein the materials are micheliolide and dimethylamine.

Specifically, the invention provides a method of producing a compound of formula (III), comprising: reacting materials, solvent and catalyst to obtain the target compound, wherein, the materials are micheliolide and propionylchloride, the catalyst is triethylamine, and the solvent is $CH_2Cl_2$.

Specifically, the invention provides a method of producing a compound of formula (IV), comprising: reacting materials and solvent to obtain the target compound, wherein, the materials are micheliolide and 3-chloroperbenzoic acid, the solvent is $CH_2Cl_2$.

Specifically, the invention provides a method of producing a compound of formula (V), comprising: dissolving material in $CH_2Cl_2$, wherein the material is a compound of formula (V);

adjusting the pH to 4-5 by using of hydrochloric acid;

lyophilizing the aqueous solution to obtain the target compound.

The invention also provides a usage of the compound or salt thereof of formula (I) for curing a cancer, wherein, the cancer includes leukemia, breast cancer, prostate cancer, nasopharyngeal carcinoma, colorectal cancer, lung cancer, liver cancer, esophageal carcinoma, gastric cancer, intestinal cancer, renal carcinoma, oral cavity cancer, Hochkin lymphoma, pancreas cancer, colorectal cancer, cervical cancer, Non Hochkin lymphoma, giiomas, melanoma, bladder carcinoma, ovarian cancer, thyroid carcinoma, Kaposi's sarcoma.

The invention also provides a usage of the compound or salt thereof of formula (I) for cancer auxiliary treatment, wherein, the cancer includes leukemia, breast cancer, Prostate cancer, nasopharyngeal carcinoma, colorectal cancer, lung cancer, liver cancer, esophageal carcinoma, gastric cancer, intestinal cancer, renal carcinoma, oral cavity cancer, Hochkin lymphoma, pancreas cancer, colorectal cancer, cervical cancer, Non Hochkin lymphoma, giiomas, melanoma, bladder carcinoma, ovarian cancer, thyroid carcinoma, Kaposi's sarcoma.

The invention also provides a usage of the compound or salt thereof of formula (I) in a drug, wherein, the drug is used for cancer medical treatment, and the cancer includes leukemia, breast cancer, Prostate cancer, nasopharyngeal carcinoma, colorectal cancer, lung cancer, liver cancer, esophageal carcinoma, gastric cancer, intestinal cancer, renal carcinoma, oral cavity cancer, Hochkin lymphoma, pancreas cancer, colorectal cancer, cervical cancer, Non Hochkin lymphoma, giiomas, melanoma, bladder carcinoma, ovarian cancer, thyroid carcinoma, Kaposi's sarcoma.

The invention also provides a usage of the compound or salt thereof of formula (I) in a drug, wherein, the drug is used for cancer auxiliary medical treatment, and the cancer includes leukemia, breast cancer, Prostate cancer, nasopharyngeal carcinoma, colorectal cancer, lung cancer, liver cancer, esophageal carcinoma, gastric cancer, intestinal cancer, renal carcinoma, oral cavity cancer, Hochkin lymphoma, pancreas cancer, colorectal cancer, cervical cancer, Non Hochkin lymphoma, giiomas, melanoma, bladder carcinoma, ovarian cancer, thyroid carcinoma, Kaposi's sarcoma.

The invention also provides a pharmaceutical composition for cancer treatment, comprising an effective amount of micheliolide derivatives or salt thereof of formula (I), in combination with a pharmaceutically acceptable carrier or other anti-cancer drug.

The invention also provides usage of the compound or salt thereof of formula (II), (III), (IV), (V) for curing a cancer, wherein, the cancer includes to leukemia, breast cancer, Prostate cancer, nasopharyngeal carcinoma, colorectal cancer, lung cancer, liver cancer, esophageal carcinoma, gastric cancer, intestinal cancer, renal carcinoma, oral cavity cancer, Hochkin lymphoma, pancreas cancer, colorectal cancer, cervical cancer, Non Hochkin lymphoma, giiomas, melanoma, bladder carcinoma, ovarian cancer, thyroid carcinoma, Kaposi's sarcoma.

The invention also provides usage of the compound or salt thereof of formula (II), (III), (IV), (V) for cancer auxiliary treatment, wherein, the cancer includes leukemia, breast cancer, Prostate cancer, nasopharyngeal carcinoma, colorectal cancer, lung cancer, liver cancer, esophageal carcinoma, gastric cancer, intestinal cancer, renal carcinoma, oral cavity cancer, Hochkin lymphoma, pancreas cancer, colorectal cancer, cervical cancer, Non Hochkin lymphoma, giiomas, melanoma, bladder carcinoma, ovarian cancer, thyroid carcinoma, Kaposi's sarcoma.

The invention also provides usage of the compound or salt thereof of formula (II), (III), (IV), (V) in a drug, wherein, the drug is used for cancer medical treatment, and the cancer includes leukemia, breast cancer, Prostate cancer, nasopharyngeal carcinoma, colorectal cancer, lung cancer, liver cancer, esophageal carcinoma, gastric cancer, intestinal cancer, renal carcinoma, oral cavity cancer, Hochkin lymphoma, pancreas cancer, colorectal cancer, cervical cancer, Non Hochkin lymphoma, giiomas, melanoma, bladder carcinoma, ovarian cancer, thyroid carcinoma, Kaposi's sarcoma.

The invention also provides usage of the compound or salt thereof of formula (II), (III), (IV), (V) in a drug, wherein, the drug is used for cancer auxiliary medical treatment, and the cancer includes leukemia, breast cancer, Prostate cancer, nasopharyngeal carcinoma, colorectal cancer, lung cancer, liver cancer, esophageal carcinoma, gastric cancer, intestinal cancer, renal carcinoma, oral cavity cancer, Hochkin lymphoma, pancreas cancer, colorectal cancer, cervical cancer, Non Hochkin lymphoma, giiomas, melanoma, bladder carcinoma, ovarian cancer, thyroid carcinoma, Kaposi's sarcoma.

The invention also provides a pharmaceutical composition for cancer treatment, comprising an effective amount of micheliolide derivatives or salt thereof of formula (II), (III), (IV), (V), in combination with a pharmaceutically acceptable carrier or other anti-cancer drug.

The compounds in the embodiments of the present invention can be used directly or in the form of pharmaceutical composition as drug. The pharmaceutical compositions contain 0.1-99%, preferred 0.5-90% compounds of the present invention, and others are pharmaceutically acceptable pharmaceutical carrier and/or excipient which are harmless to animal and human or composition with other anti-cancer drug. Compositions in the embodiments of the present invention may be formulated as injection, tablet, and capsule.

The pharmaceutical carrier and excipient are a kind or many kinds of solid, semi-solid or liquid thinner and adjuvant drug. The dosage of pharmaceutical composition of the present invention may be based on unit weight. The compounds of the invention can be administrated by injection and oral form. The injection includes intravenous injection and intramuscular injection, and the oral form may be tablets and capsules.

Micheliolide derivatives or salt thereof in the embodiments of the present invention show good effect on cancer treatment, and no obvious inhibition to normal cells.

DETAILED DESCRIPTION OF THE INVENTION

The present invention is further described in detail hereinafter with reference to the accompanying drawings as well as embodiments so as to make the objective, technical scheme and merits thereof more apparent.

A compound, which is also micheliolide derivatives, provided in an embodiment of the present invention, is presented by the formula (I):

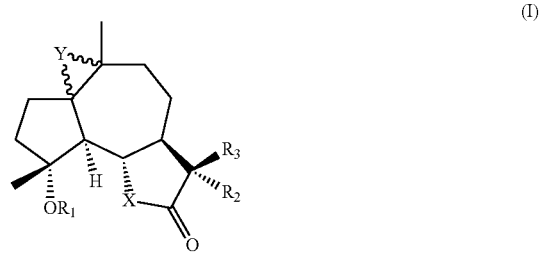

(I)

Wherein:

$R_1$ is any of H, —C(O)$R_4$ and —C(O)$R_5R_6$, wherein, $R_4$ $R_5$ and $R_6$ are any of hydrogen, alkyl, cycloalkyl, alkenyl, alkynyl, aryl, alkyaryl, arylakyl, arylalkenyl, arylalkynyl and heterocyclic respectively;

$R_3$ is hydrogen, $R_2$ is alkyl with $C_{1-8}$, containing substituent or $R_2$=$R_3$ is double bond;

X is any of O and $R_{10}$N, wherein, $R_{10}$ is any of hydrogen, alkyl, cycloalkyl, alkenyl, alkynyl, aryl, alkyaryl, arylakyl, arylalkenyl, arylalkynyl and heterocyclic;

Y is any of single bond, O, $R_{11}$N and $R_{12}R_{13}$C, wherein, $R_{11}$ is any of hydrogen, alkyl, cycloalkyl, alkenyl, alkynyl, aryl, alkyaryl, arylakyl, arylalkenyl, arylalkynyl or heterocyclic;

$R_{12}$ and $R_{13}$ are any of hydrogen, fluorine, chlorine, bromine, iodine, alkyl, cycloalkyl, alkyl substituted by hydroxyl, alkenyl, alkynyl, aryl, heterocyclic, arylakyl, arylalkenyl, arylalkynyl, cyanomethyl, alkoxy or aryloxyalkyl respectively;

Herein, $R_1$ being H, Y being single bond, and $R_2$=$R_3$ being double bond do not exist at the same time.

In an embodiment of the present invention, the substituent of the alkyl with $C_{1-8}$ comprises any of cycloalkyl, heterocycloalkyl, aryl, heteroaryl.

In an embodiment of the present invention, the substituent of the alkyl with $C_{1-8}$ comprises amino acid fragment and pharmaceutically acceptable salts thereof formed with inorganic and/or organic acid.

In an embodiment of the present invention, the substituent of the alkyl with $C_{1-8}$ comprises —$NR_7R_8$, and pharmaceutically acceptable salts thereof formed with inorganic and/or organic acid;

Wherein, $R_7$ and $R_8$ are any of hydrogen, alkyl, cycloalkyl, alkyl substituted by hydroxyl, alkenyl, alkynyl, aryl, alkyaryl, arylakyl, arylalkenyl, arylalkynyl, heterocyclic, trifluoromethyl, perfluoroalkyl, cyano, cyanomethyl, carboxyl, cabamate, sulfonyl, sulfonamide or aryloxyalkyl respectively.

In an embodiment of the present invention, the substituent of the alkyl with $C_{1-8}$ comprises —$NR_7R_8$, and pharmaceutically acceptable salts thereof formed with inorganic and/or organic acid;

Wherein, $R_7$ and $R_8$ together with N form a ring, and $R_7$ and $R_8$ are any of hydrogen, alkyl with 1 to 8 carbon atoms, any cycloalkyl respectively.

In an embodiment of the present invention, the ring comprises one or more than one substituent.

In an embodiment of the present invention, the one or more than one substituent is any of hydrogen, alkyl, cycloalkyl, alkenyl, alkynyl, aryl, alkyaryl, arylakyl, arylalkenyl, arylalkynyl and heterocyclic.

In an embodiment of the present invention, the number of the ring is three to nine.

In an embodiment of the present invention, the substituent of the alkyl with $C_{1-8}$ comprises quaternary ammonium salts formed by amino acid fragment or —$NR_7R_8$ with $R_9Z$;

Wherein, Z is any of fluorine, chlorine, bromine, iodine, tosylate, methanesulfonate, benzenesulfonate, and trifluoromethanesulfonate; R9 is any of alkyl, cycloalkyl, alkyl substituted by hydroxyl, alkenyl, alkynyl, aryl, heterocyclic, arylakyl, arylalkenyl, arylalkynyl, cyanomethyl, alkoxy or aryloxyalkyl; inorganic or organic acid are hydrofluoric acid, hydrochloric acid, hydrobromic acid, hydriodic acid, sulfuric acid, nitric acid, phosphoric acid, carbonic acid, boric acid, selenious acid, phosphomolybdic acid, phosphorous acid, sulfurous acid, citric acid, maleic acid, D-malic acid, L-malic acid, DL-malic acid, L-lactic acid, D-lactic acid, DL-lactic acid, oxalic acid, methanesulfonic acid, valeric acid, oleic acid, lauric acid, para-toluenesulfonic acid, 1-naphthalensulfonic acid, 2-naphthalensulfonic acid, phthalic acid, tartaric acid, malonic acid, succinic acid, fumaric acid, glycolic acid, thioglycolic acid, glycine, sarcocine, sulfonic acid, nicotinic acid, picolinic acid, isonicotinic acid, benzoic acid and substituted benzoic acid.

In an embodiment of the present invention, $R_2$ is methylene substituted by —$NR_7R_8$, wherein, where R7 and $R_8$ are any of hydrogen, alkyl, cycloalkyl, alkyl substituted by hydroxyl, alkenyl, alkynyl, aryl, alkyaryl, arylakyl, arylalkenyl, arylalkynyl, heterocyclic, trifluoromethyl, perfluoroalkyl, cyano, cyanomethyl, carboxyl, cabamate, sulfonyl, sulfonamide or aryloxyalkyl.

In an embodiment of the present invention, $R_2$ is methylene substituted by —$NR_7R_8$, wherein, $R_7$ and $R_8$ together with N form a ring, and $R_7$ and $R_8$ are any of hydrogen, alkyl with 1 to 8 carbon atoms, any cycloalkyl respectively.

In an embodiment of the present invention, $R_2$ is methylene substituted by amino acid fragment.

In an embodiment of the present invention, formula (I) is represented by formula (II)

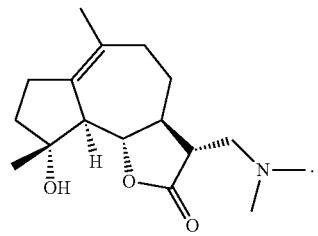

(II)

In an embodiment of the present invention, formula (I) is represented by formula (III)

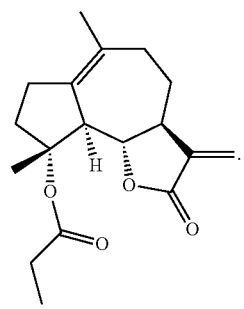

(III)

In an embodiment of the present invention, formula (I) is represented by formula (IV)

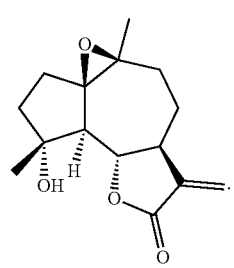

(IV)

In an embodiment of the present invention, formula (I) is represented by formula (V)

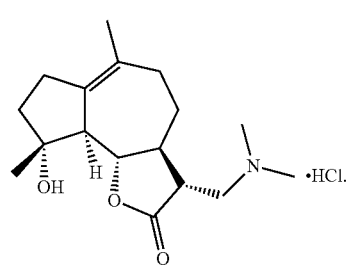

(V)

In an embodiment of the present invention, the compound disclosed above can be used in a drug, wherein the drug is used for cancer medical treatment, and the cancer comprises leukemia, breast cancer, prostate cancer, nasopharyngeal carcinoma, colorectal cancer, lung cancer, liver cancer, esophageal carcinoma, gastric cancer, intestinal cancer, renal carcinoma, oral cavity cancer, Hochkin lymphoma, pancreas cancer, colorectal cancer, cervical cancer, Non Hochkin lymphoma, giiomas, melanoma, bladder carcinoma, ovarian cancer, thyroid carcinoma, Kaposi's sarcoma.

In an embodiment of the present invention, the compound disclosed above can be in a drug, wherein the drug is used for cancer auxiliary medical treatment, and the cancer comprises leukemia, breast cancer, Prostate cancer, nasopharyngeal carcinoma, colorectal cancer, lung cancer, liver cancer, esophageal carcinoma, gastric cancer, intestinal cancer, renal carcinoma, oral cavity cancer, Hochkin lymphoma, pancreas cancer, colorectal cancer, cervical cancer, Non Hochkin lymphoma, giiomas, melanoma, bladder carcinoma, ovarian cancer, thyroid carcinoma, Kaposi's sarcoma.

In an embodiment of the present invention, a pharmaceutical composition is provided for cancer treatment, comprising an effective amount of a compound described above, in combination with a pharmaceutically acceptable carrier or other anti-cancer drug.

Embodiment 1

The Producing of 11βH,13-Dihydro, 13-dimethylaminomicheliolide (Compound II, which is Represented by Formula (II))

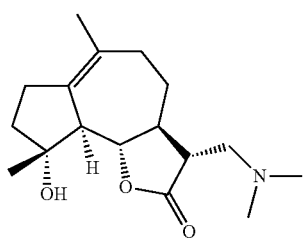

(II)

Micheliolide (106 mg, 0.40 mmol), triethylamine (2.0 mL), Me$_2$NH.HCl (41 mg, 0.5 mmol), and methanol (30 mL) are added to a 100-mL round flask. The resulting mixture is heated and refluxed for 3 hours, and then concentrated under reduced pressure to obtain crude residue which is purified by silica gel column chromatography (petroleum ether:ethyl acetate:triethylamine=50:50:0.5) to obtain 107.4 mg white solid, wherein, the yield is 86%.

Formula: $C_{17}H_{27}NO_3$

Molecular weight: 293

Properties: white amorphous powder

Spectra data:

$^1$H NMR (CDCl3, 400 MHz) δ 3.76 (t, J=10.0 Hz, 1H), 2.96 (s, 1H), 2.49-2.67 (m, 3H), 2.28-2.34 (m, 1H), 2.30-2.34 (m, 2H), 2.18 (s, 6H), 2.09 (br s, 2H), 1.96 (d, J=11.2 Hz, 1H) 1.67-1.73 (m, 2H), 1.60 (s, 3H), 1.22 (br s, 3H), 1.18 (br s, 2H); $^{13}$C NMR (CDCl$_3$, 300 MHz) δ 177.0, 131.8, 131.3, 84.0, 80.2, 58.3, 58.1, 50.9, 46.0, 44.6, 38.4, 35.3, 30.0, 27.2, 23.7, 22.8.

Embodiment 2

The Producing of 4-propionylmicheliolide (Compound III, which is Represented by Formula (III))

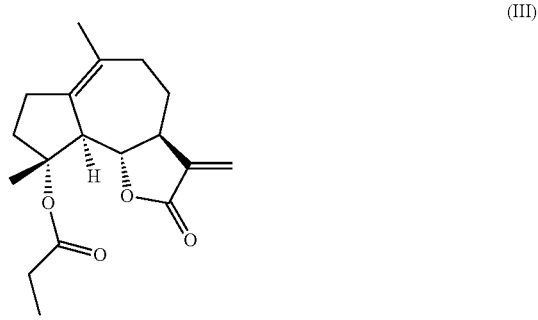

(III)

Micheliolide (106 mg, 0.40 mmol), triethylamine (2.0 mL), propionylchloride (0.2 mL) and CH$_2$Cl$_2$ (5 mL) are added to a 20-mL round flask. The resulting mixture is stirred for 3 hour at room temperature, and then concentrated under reduced pressure, and purified by using silica gel column chromatography (petroleum ether:ethyl acetate=90:10), and finally 84 mg white solid are obtained. Wherein, the yield is 72%.

Formula: $C_{18}H_{24}NO_4$

Molecular weight: 304

Properties: white amorphous powder

Spectra data:

$^1$H NMR (CDCl3, 400 MHz) δ 6.14 (s, 1H), 5.42 (s, 1H), 3.74 (t, J=10.0 Hz, 1H), 1.80-2.74 (m, 12H), 1.67 (s, 3H), 1.50 (s, 3H), 1.07 (t, J=4.0 Hz, 3H); $^{13}$C NMR (CDCl$_3$, 300 MHz) δ 173.8, 170.1, 139.5, 131.5, 130.4, 118.6, 88.4, 83.0, 56.6, 50.1, 36.5, 34.9, 30.4, 28.7, 25.9, 24.1, 18.8, 9.1.

Embodiment 3

The Producing of 1,10-Epoxymicheliolide (Compound IV, its Structure was Represented by Formula (IV))

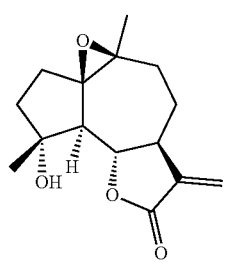

(IV)

Micheliolide (106 mg, 0.40 mmol), m-CPBA (2.0 mL), and CH$_2$Cl$_2$ (5 mL) are added to a 20-mL round flask. The resulting mixture is stirred for 6 hours at the room temperature, and then concentrated under reduced pressure, purified by using silica gel column chromatography (petroleum ether: ethyl acetate=80:20), and finally 96 mg white solid are obtained. Wherein, the yield is 91%.

Formula: $C_{15}H_{20}NO_4$
Molecular weight: 264
Properties: white amorphous powder
Spectra data:
$^1$H NMR (CDCl$_3$, 400 MHz) δ 6.13 (t, J=3.2 Hz, 1H), 5.44 (d, J=2.8 Hz, 1H), 3.73 (t, J=10.4 Hz, 1H), 1.30-2.46 (m, 11H), 1.29 (s, 3H), 1.28 (s, 3H); $^{13}$C NMR (CDCl$_3$, 300 MHz) δ 168.7, 137.8, 118.6, 79.2, 77.3, 74.2, 66.7, 52.6, 48.4, 37.1, 33.8, 29.0, 24.6, 22.5, 21.3.

Embodiment 4

The Producing of 11βH,13-Dihydro, 13-dimethylaminomicheliolide hydrochloride (Compound V, its Structure was Represented by Formula (V))

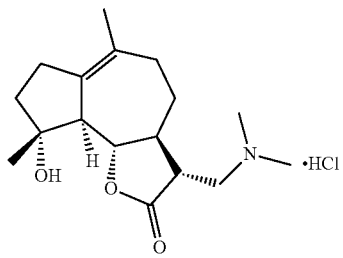

(V)

compound II (293 mg, 1 mmol) is dissolved in CH$_2$Cl$_2$ (2 mL) and was Stirred at room temperature, hydrochloric acid is added until pH=4-5. The mixture was extracted with CH$_2$Cl$_2$ (2×10 mL). The aqueous layer is lyophilized to obtain white solid, wherein, the yield is 82%. The structure data of the produced 11S,11,13-Dihydro, 13-dimethylaminomicheliolide hydrochloride are as follows:

Formula: $C_{17}H_{28}ClNO_3$
Molecular weight: 328.5
Properties: White amorphous powder
Spectra data:
$[α]_D^{20}$=−42.0 (c=10, H$_2$O); IR (KBr): 3334, 2927, 2856, 1767, 1467, 992, 967, 874, 831, 719, 669, 626, 504 cm$^{-1}$; $^1$H NMR (D$_2$O, 400 MHz) δ 4.14 (t, J=10.3 Hz, 1H), 3.51 (q, J=12.6 Hz, 1H), 3.40 (dd, J=13.3, 2.9 Hz, 1H), 3.18-3.04 (m, 1H), 2.96 (d, J=10.6 Hz, 6H), 2.67 (d, J=10.2 Hz, 1H), 2.37 (dd, J=16.2, 8.1 Hz, 1H), 2.27-2.05 (m, 4H), 1.87 (d, J=12.9 Hz, 1H), 1.73 (dd, J=19.5, 11.7 Hz, 2H), 1.66 (s, 3H), 1.46-1.31 (m, 2H), 1.26 (s, 3H); $^{13}$C NMR (CDCl$_3$, 100 MHz) δ 178.4, 132.6, 131.4, 85.1, 80.7, 56.9, 55.6, 49.9, 45.1, 42.3, 41.5, 39.2, 34.4, 29.5, 25.9, 23.2, 21.4.

Embodiment 5

The Pharmacological Activity of Micheliolide Derivatives

A variety of cancer cells are suspended to 2×10$^5$/mL, and then added into 24-hole Round-bottomed tissue culture plate. After that micheliolide and its derivatives are added, herein a test with one density occupies 5 holes. The resulting suspension are incubated (under 37° C., 5% CO$_2$) for 18 hours to allow the compounds to take effect. A absorbance (A) value is measured by using the method of MTT assay and an enzyme-linked detector under 570 nm wavelength, and then the inhibitory activity of the compounds is concluded. The result of the inhibitory activity is shown in Table 1.

TABLE 1

The inhibitory activity of micheliolide and its derivatives against different cancer cells (IC$_{50}$, nM)

| Cell lines | Compound II | Compound III | Compound IV | Compound V |
|---|---|---|---|---|
| HL-60 | 2.4 | 4.5 | 5.8 | 11.5 |
| K562 | 4.2 | 6.7 | 9.7 | 21.4 |
| MCF-7 | 4.6 | 3.4 | 8.9 | 26.8 |
| CNE-1 | 11.2 | 5.9 | 6.7 | 22.5 |
| CNE-2 | 16.5 | 12.4 | 5.6 | 16.9 |
| SW620 | 5.8 | 5.6 | 3.8 | 13.5 |
| A549 | 7.2 | 7.7 | 5.7 | 18.1 |
| HepG-2 | 4.5 | 15.4 | 7.4 | 27.9 |
| Ec9706 | 9.2 | 7.6 | 6.6 | 15.7 |
| SGC7901 | 14.6 | 14.7 | 13.4 | 24.9 |
| SW1116 | 11.5 | 21.5 | 11.7 | 31.2 |
| A498 | 12.4 | 5.3 | 4.3 | 16.3 |
| ASPC-1 | 3.9 | 15.1 | 26.4 | 33.6 |
| HT-29 | 4.8 | 9.8 | 9.8 | 19.2 |
| HeLa | 9.4 | 17.3 | 9.7 | 33.4 |
| GL15 | 12.6 | 14.3 | 21.5 | 25.8 |
| B16F1 | 3.4 | 13.2 | 5.2 | 18.6 |
| T24 | 14.2 | 13.6 | 7.9 | 22.5 |
| SKOV3 | 5.9 | 9.4 | 10.4 | 15.4 |
| SW579 | 17.3 | 22.5 | 12.4 | 32.6 |
| PC-3 | 8.7 | 11.4 | 17.2 | 23.5 |

In Table 1, HL-60, K562, MCF-7, CNE-1, CNE-2, SW620, A549, HepG2, Ec9706, SGC7901, SW1116, A498, ASPC-1, HT-29, HeLa, GL15, B16F1, T24, SKOV3, SW579, PC-3, represents acute leukemia cell lines, Chronic leukemia cell lines, Breast cancer cell lines, High differentiation nasopharyngeal carcinoma cell line, Poorly differentiated nasopharyngeal carcinoma cell lines, Colorectal cancer cell line, Lung cancer cell lines, Hepatocellular carcinoma cell lines, Esophageal cancer cell line, Gastric cancer cell line, Colon cancer cell line, Renal cell carcinoma cell line, Pancreatic cancer cell line, Colon cancer cell lines, uterine cervical cancer cell lines, Horny man neuroblastoma cell lines, Melanoma cell line, human bladder cancer cell line, ovarian cancer cell lines, thyroid cancer cells, prostate cancer cell lines, respectively.

The tested result shows the compounds show strong inhibitory activity against the tested cells, however, have no obvious inhibition against normal cells at 50 μM. Embodiment 6
Injection Compounds II, III, IV, V produced in the embodiments 1 to 4, is respectively dissolved in a small amount of DMSO. Injective water is then added into the mixed solvent and filtered finely, after potting and sterilization, finally the injection is obtained.

Embodiment 7

Tablet

The compounds II, III, IV, V produced in the embodiments 1 to 4, is mixed respectively with excipients according to weight ratio of 5:1, and then tableted to obtain tablets.

Embodiment 8

Capsule he compounds II, III, IV, V prepared in the Examples 1-4, is mixed respectively with excipients according to weight ratio of 5:1 to obtain capsules.

The compounds, usage and producing methods of the present invention have been described with specific embodiments. It is obviously for those skilled in the art to appropriately change raw materials, process conditions et al, to achieve corresponding purposes. The changes are still in the scope of the present invention. Any modification, equivalent replacement and improvement made without departing from the spirit and principle of the present invention should be included within the protection scope thereof.

The invention claimed is:

1. A compound of the formula (I):

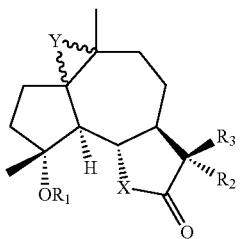

(I)

wherein:

R$_1$ is H;

R$_3$ is hydrogen, R$_2$ is methylene substituted by —NR$_7$R$_8$, and its pharmaceutically acceptable salts formed with at least one of inorganic and organic acid;

wherein R$_7$ and R$_8$ are selected from hydrogen, alkyl having in the range of 1 up to 8 carbon atoms;

wherein the inorganic and organic acid are selected from hydrofluoric acid, hydrochloric acid, hydrobromic acid, hydriodic acid, sulfuric acid, nitric acid, phosphoric acid, carbonic acid, boric acid, selenious acid, phosphomolybdic acid, phosphorous acid, sulfurous acid, citric acid, maleic acid, D-malic acid, L-malic acid, DL-malic acid, L-lactic acid, D-lactic acid, DL-lactic acid, oxalic acid, methanesulfonic acid, valeric acid, oleic acid, lauric acid, para-toluenesulfonic acid, 1-naphthalensulfonic acid, 2-naphthalensulfonic acid, phthalic acid, tartaric acid, malonic acid, succinic acid, fumaric acid, glycolic acid, thioglycolic acid, glycine, sarcocine, sulfonic acid, nicotinic acid, picolinic acid, isonicotinic acid, and benzoic acid;

wherein X is O;

Y is a single bond.

2. A compound according to claim 1, wherein, formula (I) is represented by formula (II)

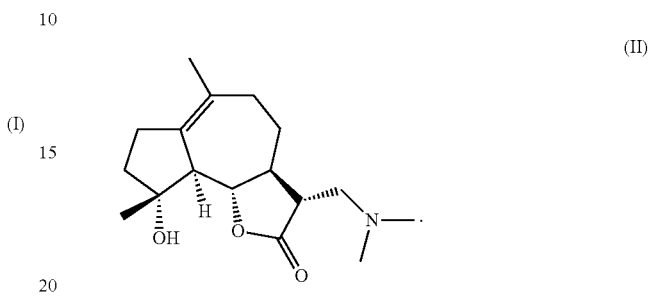

(II)

3. A compound according to claim 1, wherein, formula (I) is represented by formula (V)

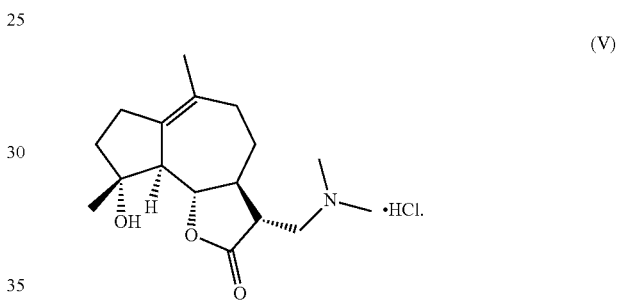

(V)

4. A pharmaceutical composition for cancer treatment, comprising an effective amount of a compound of claim 1, in combination with a pharmaceutically acceptable carrier.

* * * * *